(12) United States Patent
Gentalen et al.

(10) Patent No.: US 6,852,490 B2
(45) Date of Patent: Feb. 8, 2005

(54) METHODS OF USING AN ARRAY OF POOLED PROBES IN GENETIC ANALYSIS

(75) Inventors: Erik Gentalen, Redwood City, CA (US); Mark Chee, Del Mar, CA (US)

(73) Assignee: Affymetrix, Inc., Santa Clara, CA (US)

( * ) Notice: Subject to any disclaimer, the term of this patent is extended or adjusted under 35 U.S.C. 154(b) by 48 days.

(21) Appl. No.: 09/930,536

(22) Filed: Aug. 14, 2001

(65) Prior Publication Data

US 2002/0106663 A1 Aug. 8, 2002

Related U.S. Application Data

(63) Continuation of application No. 09/138,958, filed on Aug. 24, 1998, now Pat. No. 6,306,643.

(51) Int. Cl.[7] .......................... C12Q 1/68; C12P 19/34; C12M 1/34; C07H 21/02; C07H 21/04
(52) U.S. Cl. .......................... 435/6; 435/7.1; 435/91.1; 435/91.2; 435/257.2; 536/22.1; 536/23.1; 536/24.3; 536/24.31; 536/24.32; 536/24.33
(58) Field of Search .......................... 435/6, 7.1, 91.1, 435/91.2, 287.2; 526/22.1, 23.1, 24.3–24.33

(56) References Cited

U.S. PATENT DOCUMENTS

| | | | |
|---|---|---|---|
| 5,202,231 A | | 4/1993 | Drmanac et al. |
| 5,492,806 A | | 2/1996 | Drmanac et al. |
| 5,525,464 A | | 6/1996 | Drmanac et al. |
| 5,614,388 A | | 3/1997 | Picone et al. |
| 5,667,972 A | | 9/1997 | Drmanac et al. |
| 5,695,940 A | | 12/1997 | Drmanac et al. |
| 5,700,637 A | | 12/1997 | Southern |
| 5,858,659 A | | 1/1999 | Sapolsky et al. |
| 6,013,449 A | * | 1/2000 | Hacia et al. .................... 435/6 |
| 6,040,138 A | | 3/2000 | Lockhart et al. |
| 6,103,463 A | * | 8/2000 | Chetverin et al. ............. 435/6 |
| 6,306,643 B1 | * | 10/2001 | Gentalen .................. 435/287.2 |
| 6,312,892 B1 | * | 11/2001 | Barany et al. ................... 435/6 |

FOREIGN PATENT DOCUMENTS

| | | |
|---|---|---|
| EP | 235 726 | 5/1989 |
| EP | 717 113 | 7/1996 |
| EP | 0 721 016 A2 | 7/1996 |
| WO | WO 89/11548 | 11/1989 |
| WO | WO95/11995 | * 5/1995 |
| WO | WO 95/11995 | 5/1995 |
| WO | WO 97/46313 A1 | 12/1997 |
| WO | WO 98/11210 A1 | 3/1998 |
| WO | WO 98/41657 A1 | 9/1998 |
| WO | WO 98/53103 A1 | 11/1998 |

OTHER PUBLICATIONS

Chee, Mark, et al.; Accessing Genetic Information with High–Density DNA Arrays; XP 002022508.
Copy of European Search Report for EP 99 94 2387.
Bains et al., "A Novel Method for Nucleic Acid Sequence Determination," *J. Theor. Biol.*, 135(3):303–307 (1988).

* cited by examiner

*Primary Examiner*—Jeffrey Siew
(74) *Attorney, Agent, or Firm*—Townsend and Townsend and Crew LLP

(57) ABSTRACT

The invention provides arrays of polynucleotide probes having at least one pooled position. A typical array comprises a support having at least three discrete regions. A first region bears a pool of polynucleotide probes comprising first and second probes. A second region bears the first probe without the second probe and a third region bears the second probe without the first probe. A target nucleic acid having segments complementary to both the first and second probes shows stronger normalized binding to the first region than to the aggregate of binding to the second and third regions due to cooperative binding of pooled probes in the first region. The invention provide methods of using such arrays for e.g., linkage analysis, sequence analysis, and expression monitoring.

10 Claims, 8 Drawing Sheets

METHODS OF USING AN ARRAY OF POOLED PROBES IN GENETIC ANALYSIS

This application is a continuation of U.S. patent application Ser. No. 09/138,958, filed Aug. 24, 1998, now U.S. Pat. No. 6,306,643, which is incorporated herein by reference.

STATEMENT OF GOVERNMENT INTEREST

This work was, in part, supported by NIH grant # 5P0 1HG01 323, and the US Government may have certain rights in this invention.

BACKGROUND

Arrays of oligonucleotide probes have been used in a variety of methods for analyzing target nucleic acids of interest. One such application involves de novo sequencing of a target nucleic acid. Such can, at least in theory, be achieved by hybridizing a target nucleic acid to a complete array of all probe sequences of a given length and identifying the subset of probes that hybridize to the target. Another application is the detection and quantification of mRNA levels in a mixed population. Other applications involve comparing a known reference sequence with a target sequence that may differ from the reference sequence in the presence of mutations, polymorphisms and other variations.

A simple strategy for identifying variations in a target sequence is the reverse dot blot, as discussed by Dattagupta, EP 235,726, Saiki, WO 89/11548. Other strategies for comparative analysis of target nucleic acids with reference nucleic acids are described in WO 95/11995 (incorporated by reference in its entirety for all purposes). Some such arrays include four probe sets. A first probe set includes overlapping probes spanning a region of interest in a reference sequence. Each probe in the first probe set has an interrogation position that corresponds to a nucleotide in the reference sequence. That is, the interrogation position is aligned with the corresponding nucleotide in the reference sequence, when the probe and reference sequence are aligned to maximize complementarily between the two. For each probe in the first set, there are three corresponding probes from three additional probe sets. Thus, there are four probes corresponding to each nucleotide in the reference sequence. The probes from the three additional probe sets are identical to the corresponding probe from the first probe set except at the interrogation position, which occurs in the same position in each of the four corresponding probes from the four probe sets, and is occupied by a different nucleotide in the four probe sets.

Such an array is hybridized to a labelled target sequence, which may be the same as the reference sequence, or a variant thereof. The identity of any nucleotide of interest in the target sequence can be determined by comparing the hybridization intensities of the four probes having interrogation positions aligned with that nucleotide. The nucleotide in the target sequence is the complement of the nucleotide occupying the interrogation position of the probe with the highest hybridization intensity.

A further strategy for comparing a target sequence with a reference sequence is described in EP 717,113. In this strategy, an array contains overlapping probes spanning a region of interest in a reference sequence. The array is hybridized to a labelled target sequence, which may be the same as the reference sequence or a variant thereof. If the target sequence is a variant of the reference sequence, probes overlapping the site of variation show reduced hybridization intensity relative to other probes in the array. In arrays in which the probes are arranged in an ordered fashion stepping through the reference sequence (e.g., each successive probe has one fewer 5' base and one more 3' base than its predecessor), the loss of hybridization intensity is manifested as a "footprint" of probes approximately centered about the point of variation between the target sequence and reference sequence.

In most of the array strategies described above, each probe present in an array occupies a unique cell or region of the array. In this arrangement, the signal bound by each probe is separately determinable. However, Bains & Smith, J. Theor. Biol. 135, 303–307 (1988) discuss a method of sequencing by hybridization employed an array of oligonucleotides six nucleotides long, in which the two central positions are occupied by pools of each of the four nucleotide bases. In other words, a cell of such an array is occupied by a mixture of sixteen probes of related sequence. The sixteen probes share four positions and differ at two central positions. WO 95/11995 also describes some arrays containing pooled mixtures of probes. These pooled probes have component probes that are complementary to a common segment of a target sequence except at one or a few positions within the probe lengths at which the probes differ. Such probes can be used in several strategies to detect variations in a target sequence relative to a reference sequence. These pooling strategies can have advantages in reducing the number of array cells required to analyze a given target sequence.

SUMMARY OF THE CLAIMED INVENTION

The invention provides arrays of polynucleotide probes bound to a support having at least one pooled position. Some such arrays comprise a support having at least three discrete regions. A first region bears a pool of polynucleotide probes comprising first and second probes. A second region bears the first probe without the second probe and a third region bears the second probe without the first probe. In some arrays, the first and second probes are respectively complementary to first and second nonoverlapping segments of a target sequence. In some arrays, the first and second nonoverlapping segments of the target nucleic acid respectively contain first and second polymorphic sites, and the first probe is complementary to a polymorphic form of the first site and the second probe is complementary to a polymorphic form of the second site.

In some arrays, the second region bears the first probe with a third probe as a second pool of polynucleotide probes, and the third region bears the second probe with a fourth probe, as a third pool of polynucleotide probes. In some arrays, the third probe is complementary to a second polymorphic form of the second polymorphic site, and the fourth probe is complementary to a second polymorphic form of the first polymorphic site.

Some array comprise a substrate having a plurality of discrete regions, the different regions bearing different pools of probes. A pool of probes comprises first and second probes complementary to nonoverlapping segments of a target sequence. In some such arrays, the nonoverlapping segments of the target sequence include first and second polymorphic sites and the first and second probes are respectively complementary to polymorphic forms of the first and second polymorphic sites, the different pools comprising probes complementary to different combinations of polymorphic forms, the different pools differing in the combination of polymorphic forms. In some arrays, the first probe is the same in at least a subset of the plurality of pools and the second probe varies in different pools in the subset. In some arrays, the pool of probes comprises first and second subsets of probes. Each pool in the first subset of pools has a common first probe and a different second probe. Each pool in the second subset of pools has a common first probe and a different second probe, and the common first probe differs between the first subset of pools and the second subset of pools.

The invention further provides arrays comprising a support having at least three discrete regions. A first region bears a pool of polynucleotide probes comprising first and second probes at a first molar ratio of first to second probes. A second region bearing the first probe without the second probe or with the second probe present at a second molar ratio of first probe to second probe greater than first molar ratio. A third region bears the second probe without the first probe or with the first probe present at a third molar ratio of first probe to second probe less than the first molar ratio.

The invention further provides methods of determining linkage of polymorphic forms in a target nucleic acid. Such methods entail hybridizing a diploid target nucleic acid having first and second polymorphic sites to an array comprising a support having at least three discrete regions. A first region bears a pool of polynucleotide probes comprising a first probe complementary to a polymorphic form of the first polymorphic site and a second probe complementary to a polymorphic form of the second polymorphic site. A second region bears the first probe without the second probe and a third region bears the second probe without the first probe. The next step is to determine a ratio of binding of the target nucleic acid to the first region and to the second and third regions combined to indicate whether the polymorphic form of the first polymorphic site and the polymorphic form of the second polymorphic site are present in the same molecule of the diploid target nucleic acid.

The invention provides additional methods of determining linkage of polymorphic forms in a target nucleic acid. Such methods entail hybridizing a diploid target nucleic acid having first and second polymorphic sites to an array comprising a support having a plurality of discrete regions, the different regions bearing different pools of probes, a pool of probe comprising first and second probes respectively complementary to polymorphic forms of the first and second polymorphic sites, the different pools comprising probes complementary to different combinations of polymorphic forms. Binding of the target nucleic acid to the discrete regions is then determined to identify at least one discrete region that binds more target nucleic acid than an average of target nucleic acid bound by the discrete regions, the at least one discrete region bearing a pool of probes respectively complementary to a combination of polymorphic forms present in a single molecule of the diploid target nucleic acid. Some such methods, further comprise hybridizing a control mixture of a first nucleic acid having a polymorphic form at the first polymorphic site and a second nucleic acid having a polymorphic form at the second polymorphic site and determining hybridization of the mixture to the discrete regions. Binding of the control region to the discrete regions is then determined. One then compares binding of the target nucleic acid and control to the discrete regions to identify a discrete region binding more strongly to the target nucleic acid than the control, this discrete region bearing a pool of probes respectively complementary to a combination of polymorphic forms present in a single molecule of the diploid target nucleic acid.

The invention further provides methods of sequencing a target nucleic acid. Such methods entail hybridizing the target nucleic acid to an array comprising a substrate having a plurality of discrete regions bearing different pools of probes, each pool having a common first probe and a different second probe, the common first probe complementary to a known marker in the target. A sequence of a segment of the target nucleic acid is then determined from the relative binding of the target nucleic acid to the pools of probes. The position of the segment in the target sequence is then mapped relative to the known marker.

Other sequencing methods entail hybridizing a target nucleic acid to an array comprising a substrate having a plurality of discrete regions, different regions bearing different pools of probes, wherein the pools are subdivided into first and second subarray of pools, each pool in the first subarray of pools having a common first probe and a different second probe, each pool in the second subarray of pools having a common first probe complementary to a known marker in the target, and a different second probe, the common first probe in the first subarray of pools being complementary to a different known marker than in the second subarray of pools. A sequence of first and second segment of target nucleic acid is then determined from the binding of the target nucleic acid to the pools in the first and second subarrays. The position of first and second segments in the target nucleic acid is then mapped relative to the positions of the known markers.

The invention further provides methods of monitoring expression of an mRNA population. Such methods entail providing a sample comprising a population of MRNA molecules. The population of mRNA or nucleic acids copied therefrom is then hybridized to an array comprising a support having a plurality of discrete regions, the different regions bearing different pools of probes, a pool of probe comprising first and second probes respectively complementary to nonoverlapping segments of a known MRNA molecule, the different pools comprising first and second probes complementary to nonoverlapping segments from different known MRNA molecules. One then determines which discrete regions show specific binding to the population thereby indicating which of the known mRNA molecules are present in the sample.

In some such methods, the support further comprises a second plurality of discrete regions, the different regions bearing different pools of probes, each pool having the same first and second probes except for a single base mismatch in the first or second probe or both as a corresponding pool from the plurality of discrete regions, and the method further comprises comparing binding of corresponding pools of probes from the plurality and second plurality of discrete regions, a difference in binding indicating that the known MRNA to which probes in the pool from the plurality of discrete regions are complementary is present in the sample.

The invention further provides methods of analyzing target nucleic acid. Such methods entail hybridizing a target nucleic acid to an array comprising a support having at least three discrete regions, a first region bearing a pool of polynucleotide probes comprising first and second probes, a second region bearing the first probe without the second probe and a third region bearing the second probe without the first probe. One then compares binding of the target nucleic acid to the first discrete region with the aggregate of the target nucleic acid binding to the second and third regions to determine whether the target nucleic acid includes segments complementary to the first and second probes.

BRIEF DESCRIPTION OF THE FIGURES

FIG. 4B 50:50 mixtures of (10c-27t and 10g-27c) (SEQ ID NO:1) and (10g-27t and 10c-27c) (SEQ ID NO:1) are shown in the two panels of the left hand column. Although the two experiments have targets that are identical in sequence composition, the pairing is different. This is clearly detected in the experiment, which allows the pairings (linkages) to be determined in each case. The bottom panel in the right hand column shows a hybridization image of (10c, 10g, 27c, and 27t). The sequence composition is identical to the two lower panels of the left hand column. However, in this case the individual targets are unlinked, and hence no cooperative effect is observed.

DEFINITIONS

Figure 1:
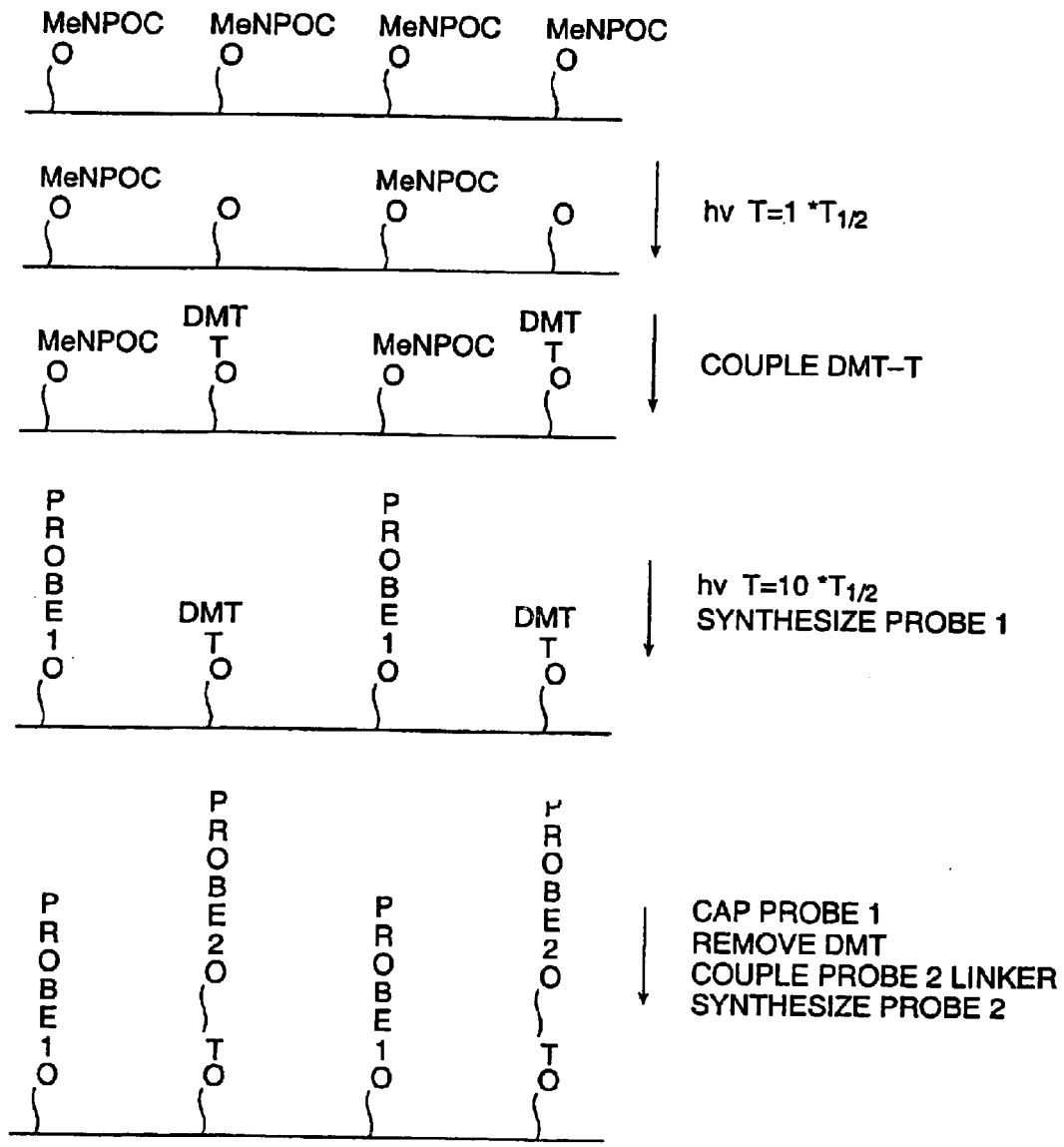
FIG. 1. Synthesis of paired probe arrays. Firstly, a 1:1 mixture of photoprotected and DMT protected linkers is created over the entire surface of the array. This is accomplished by irradiating a MeNPOC-linker photoprotected glass surface with 365 nm UV light, such that half the sites are deprotected ($T_{1/2}$=half life of the MeNPOC group). The deprotected sites are reacted with a 5' DMT protected nucleoside. Next, the first probe sequence is synthesized at each location on the array: the remaining MeNPOC sites are deprotected, and standard light-directed oligonucleotide synthesis is carried out at these sites. When the first probe synthesis has been completed, the 5' ends are capped. Finally, the second probe sequence is synthesized. Acid deprotection is used to make available the sites previously reserved by DMT protection. After the addition of a photoprotected linker, standard light-directed oligonucleotide synthesis is then used to prepare the second probe sequence.

A nucleic acid is a deoxyribonucleotide or ribonucleotide polymer in either single-or double-stranded form, including known analogs of natural nucleotides unless otherwise indicated.

An oligonucleotide is a single-stranded nucleic acid ranging in length from 2 to about 500 bases. An oligonucleotide can be synthetic or natural.

A probe is an oligonucleotide capable of binding to a target nucleic acid of complementary sequence through one or more types of chemical bonds, usually through complementary base pairing, usually through hydrogen bond formation. An oligonucleotide probe may include natural (i.e. A, G, C, or T) or modified bases (e.g., 7-deazaguanosine, inosine). In addition, the bases in oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages. Probes are typically about 10–50 bases long, and are often 15–20 bases. The length of probes used as components of pools for hybridization to distal segments of a target sequence often increases as the spacing of the segments increased thereby allowing hybridization to be conducted under greater stringency to increase discrimination between matched and mismatched pools of probes.

Specific hybridization refers to the binding, duplexing, or hybridizing of a molecule only to a particular nucleotide sequence under stringent conditions when that sequence is present in a complex mixture (e.g., total cellular) DNA or RNA. Stringent conditions are conditions under which a probe will hybridize to its target subsequence, but to no other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide or tetraalkyl ammonium salts. For example, conditions of 5X SSPE (750 mM NaCl, 50 mM NaPhosphate, 5 mM EDTA, pH 7.4) and a temperature of 25–30° C. are suitable for allele-specific probe hybridizations.

A perfectly matched probe has a sequence perfectly complementary to a particular target sequence. Such a probe is typically perfectly complementary to a portion (subsequence) of the target sequence. The term "mismatch probe" refer to probes whose sequence is deliberately selected not to be perfectly complementary to a particular target sequence. Although the mismatch(es) may be located anywhere in the mismatch probe, terminal mismatches are less desirable as a terminal mismatch is less likely to prevent hybridization of the target sequence. Thus, probes are often designed to have the mismatch located at or near the center of the probe such that the mismatch is most likely to destabilize the duplex with the target sequence under the test hybridization conditions.

A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

A pool probe mixture is a mixture of two or more probes occupying a single discrete cell of an array. Although the identity of each probe in the mixture is known, the individual probes in the pool are not separately addressable. Thus, the hybridization signal from a cell bearing a pool probe mixture is the aggregate of that of the different probes occupying the cell.

When one cell is said to be occupied by a first probe without a second probe, typically the second probe is entirely absent from the cell, although trace amounts of the second probe (e.g., less than 10% molecules relative to the first probe) can sometimes be tolerated.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the combination ac to occur with a frequency of 0.25. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be used detected to indicate susceptibility to the disease in circumstances in which the gene Y may not have been identified or may not be readily detectable.

DETAILED DESCRIPTION

1. General

The invention is premised, in part, on the result that two different probes in a pooled mixture of probes can simultaneously hybridize to different segments of the same target molecule in a co-operative manner. In consequence, the binding of a target to a pool of two mixed probes is greater than the sum of binding of the target to the same two probes separated in individual cells in an array. In the latter arrangement, each of the two probes can bind to its respective complementary segment in a target sequence, but the two probes cannot simultaneously bind to the same target molecule. The observed cooperative binding of pooled probes can be employed in several methods of analysis that distinguish between a single target molecule containing two segments of interest, and two target molecules, each containing one of the segments of interest. Applications include increasing the specificity of hybridization in mutation detection and gene expression monitoring applications, determining SNP haplotypes, characterizing repetitive sequences, such as short tandem repeats, and aiding contig assembly in sequencing by hybridization (SBH).

In a simple illustration of such methods, an array of probes is designed having three cells. One cell contains a pooled mixture of first and second probes respectively complementary to first and second segments of interest in potential target molecules. A second cell in the array contains the first probe without the second probe, and a third cell contains the second probe without the first probe.

The array is initially hybridized with a control equimolar mixture of first and second target molecules respectively containing the first and second target segments (but not both). Typically, the target sequences are labelled. Binding of target to different cells in the array can thus be determined by scanning the label. The binding is separately determined for each of the three cells, and a ratio is calculated for binding to the first cell (pooled probes) with the sum of binding to the second and third cells. In idealized circumstances, since cooperative binding of pooled probes to separate target molecules is not possible, one might expect that the ratio of binding might be one. However, in practice, the binding ratio often varies from one due to factors such as variation in probe deposition between cells and steric crowding of probes in the pooled cells. Thus, a normalization factor can be calculated to convert the observed binding ratio to unity.

The array is then hybridized with an unknown target sample, which may be either a single target molecule containing both first and second segments, or two separate molecules, the first of which contains the first segment only, and the second of which contains the second segment only. Again, the ratio of binding of the target to the first cell relative to the combined binding to second and third cells is determined. If appropriate, the normalization factor is applied. A ratio of binding (normalized, if appropriate) greater than unity indicates that the sample contains a single molecule containing both first and second segments of interest. Typically, a single molecule containing both first and second segments give a normalized ratio at least two fold higher than a mixture of separate molecules, each containing one of the segments.

In some methods, multiple cells in the array contain different pooled mixtures of probes. Such arrangements are particularly useful for analyzing targets that can have multiple combinations of segments. For example, a target nucleic acid having two-polymorphic sites, each of which has two polymorphic forms (A/a and B/b) can have four combinations of polymorphic forms AB, aB, ab, and Ab). To analyze such a target sequence, an array is designed with four cells each containing a different pool of two mixed probes. The two probes in each pool are designed to be complementary to one of the combinations of polymorphic forms (i.e., A'B', a'B', a'b', and A'b', where primes indicate complementary sequences). When such an array is hybridized with a target sample containing a single target nucleic acid, the pool of probes having both component probes matched with the target nucleic acid shows highest binding, two pools of probes having one probe but not the other matched with the target nucleic acid show intermediate binding, and the pool of probes having neither probe matched with the target shows the lowest binding.

When such an array is hybridized with a mixture of two target molecules containing different combinations of polymorphic forms at the two sites, as in a sample from a diploid organisms, a different pattern results. In this situation, two pooled probes have both component probes matched with the same target molecule and gives the highest binding signal. The other two pools may have only one component probe matched with a target segment or can have both component probes matched with segments on different molecules of target sequence. In the latter situation, the two component probes in each pool are matched with different molecules of target sequence, and cooperative binding is not possible. Thus, the binding of pooled probes not matched with a single target molecules is lower that for the two pools of probes having both probes matched with the same target molecule. The observed relative binding of the four probe thus serves to indicate which of the combination(s) of polymorphic forms are present in a target sample.

2. Target sequences

A target sequence is either a known sequence or a variant of a known or partly known reference sequence. A target sequence often encodes a gene or part of a gene. Often the target sequence contains one or more known polymorphic sites. The function of the target sequence may or may not be known. Target sequences of interest include human genes associated with genetic disease. Examples of such genes include BRCA-1, BRCA-2, p53, N-, C- and K-ras, cytochromes P450, CFTR, HLA classes I and II, and β-globin.

The target nucleic acid can be genomic, RNA or cDNA. Genomic DNA samples are usually subject to amplification before application to an array using primers flanking the region of interest. Genomic DNA can be obtained from virtually any tissue source (other than pure red blood cells). For example, convenient tissue samples include whole blood, semen, saliva, tears, urine, fecal material, sweat, buccal, skin and hair. Amplification of genomic DNA containing a polymorphic site generates a single species of target nucleic acid if the individual from the sample was obtained is homozygous at the polymorphic site or two species of target molecules if the individual is heterozygous.

RNA samples are also often subject to amplification. In this case amplification is typically preceded by reverse transcription. Amplification of all expressed mRNA can be performed as described by commonly owned WO 96/14839 and WO 97/01603. Amplification of an RNA sample from a diploid sample can generate two species of target molecule if the individual from whom the sample was obtained is heterozygous at a polymorphic site occurring within expressed RNA.

The PCR method of amplification is described in *PCR Technology: Principles and Applications for DNA Amplification* (ed. H. A. Erlich, Freeman Press, N.Y., N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202 (each of which is incorporated by reference for all purposes). Nucleic acids in a target sample are usually labelled in the course of amplification by inclusion of one or more labelled nucleotides in the amplification mix. Labels can also be attached to amplification products after amplification e.g., by end-labelling. The amplification product can be RNA or DNA depending on the enzyme and substrates used in the amplification reaction.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA,* 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

A variety of labels can be incorporated into target nucleic acids in the course of amplification or after amplification. Suitable labels include fluorescein or biotin, the latter being detected by staining with phycoerythrin-streptavidin after hybridization. In some methods, hybridization of target nucleic acids is compared with control nucleic acids. Optionally, such hybridizations can be performed simultaneously using different labels are used for target and control samples. Control and target samples can be diluted, if desired, prior to hybridization to equalize fluorescence intensities.

3. Supports

Supports can be made of a variety of materials, such as glass, silica, plastic, nylon or nitrocellulose. Supports are preferably rigid and have a planar surface. Supports typically have from 1–10,000,000 discrete spatially addressable regions, or cells. Supports having 10–1,000,000 or 100–100,000 or 1000–100,000 cells are common. The density of cells is typically at least 1000, 10,000, 100,000 or 1,000,000 cells within a square centimeter. In some supports, all cells are occupied by pooled mixtures of probes. In other supports, some cells are occupied by pooled mixtures of probes, and other cells are occupied, at least to the degree of purity obtainable by synthesis methods, by a single type of oligonucleotide. The strategies for probe design described in the present application can be combined with other strategies, such as those described by WO 95/11995, EP 717,113 and WO 97/29212 in the same array.

Typically, the component probes of a pool are present in the pool in equimolar ratio. However, in some arrays, some pools have more of one probe than other. For example, an array can be designed in which one region has an equimolar region of first and second probes, a second region has the first probe and second probes present with the first probe in excess, and a third region has the first and second probes present with the second probes in excess. In general, a target bearing first and second segments complementary to the first and second probes shows stronger normalized binding to the first region than the aggregate of binding to the second and third regions. Some arrays also include regions occupied by single probes. Within such regions the single probe is substantially pure (i.e., at least 90%, 95%, 99% or 99.9% or 100% pure on molar basis) other than for incomplete synthesis intermediates.

4. Synthesis of probe arrays

Arrays of probes can be synthesized in a step-by-step manner on a support or can be attached in presynthesized form. A preferred method of synthesis is VLSIPS$^{TM}$ (see Fodor et al., 1991, Fodor et al., 1993, Nature 364, 555–556; McGall et al., U.S. Ser. No. 08/445,332; U.S. Pat. No. 5,143,854; EP 476,014), which entails the use of light to direct the synthesis of oligonucleotide probes in high-density, miniaturized arrays. Algorithms for design of masks to reduce the number of synthesis cycles are described by Hubbel et al., U.S. Pat. No. 5,571,639 and U.S. Pat. No. 5,593,839. Arrays can also be synthesized in a combinatorial fashion by delivering monomers to cells of a support by mechanically constrained flowpaths. See Winkler et al., EP 624,059. Arrays can also be synthesized by spotting monomers reagents on to a support using an ink jet printer. See id.; Pease et al., EP 728,520.

The basic VLSIPS$^{TM}$ approach can readily be adapted to synthesize pooled mixtures of probes. The component probes of a pool are synthesized in series. Synthesis of a pooled probes starts with a substrate covered with a photo-sensitive protective group. The group is partially removed by limited exposure of substrate to light. The deprotected sites are capped with a protective group that is nonphotosentive but can be removed by other means, such as a chemical solvent. The remaining sites are then exposed to more light removing the remaining photosensitive protective groups. Synthesis proceeds on the exposed sites in a step-by-step fashion until first members of pooled probes are synthesized. The nonphotosensitive capping groups are then removed. Synthesis proceeds anchored from these sites in a step-by-step fashion until second members of pooled probes are formed. After hybridization of control and target samples to an array containing one or more probe sets as described above and optional washing to remove unbound and non-specifically bound probe, the hybridization intensity for the respective samples is determined for each probe in the array. For fluorescent labels, hybridization intensity can be determined by, for example, a scanning confocal microscope in photon counting mode. Appropriate scanning devices are described by e.g., Trulson et al., U.S. Pat. No. 5,578,832; Stern et al., U.S. Pat. No. 5,631,734 and are available from Affymetrix, Inc. under the GeneChip$^{TM}$ label. Some types of label provide a signal that can be amplified by enzymatic methods (see By making use of enzymatic methods of mismatch discrimination[13].

5. Methods of Use a. Linkage Analysis

Grouping and ordering genomic DNA markers is used to make physical and genetic maps, and to establish the relationship between genotype and phenotype. Markers in close proximity on the same DNA molecule tend to be inherited together, because the likelihood of a recombination event between two markers decreases as their separation decreases. The quantitative measurement of this phenomenon and its application to genetic analysis, was pioneered by Sturtevant in 1913[1]. Since then, a wide variety of genetic and molecular mapping techniques have been developed and used to build genomic maps based on both genetic and physical DNA markers. Recombination-based mapping has been supplemented by molecular techniques, such as radiation hybrid mapping [2], and methods that are based on single chromosome copy analysis [3], [4], [5], or allele-specific detection, [6], [7]. Other methods for establishing linkage include direct visualization of markers, using, for example, electron microscopy and fluorescence in situ hybridization (FISH) [8], [9].

In the present methods, linkage is determined using arrays containing cells occupied by pooled probes. Targets for linkage analysis are typically known sequences containing at least two polymorphic sites. The target sequences may or may not have previously been characterized for a function. The polymorphic sites are typically from 10–100,000, 50–10,000 or 100–5000 bases apart. As indicated above, an array for analyzing such a target sequence contains mixtures of pooled probes corresponding to different combinations of polymorphic forms at the target. If a target contains two polymorphic sites, one probe in a pool is typically an allele specific probe overlapping one of the sites and complementary to one of the polymorphic forms at this site. The other probe in the same pool is typically an allele specific probe that overlaps the other polymorphic site in the target sequence and is complementary to a polymorphic form at that allele. If a target sequence contains two polymorphic sites and two polymorphic forms are present at each site, there are four possible combinations of polymorphic forms, and four pools or probes are required.

If a target sequence contains two polymorphic sites and there are three polymorphic forms at each site, then there are nine combinations of polymorphic forms and nine pools of probes are required. If a target sequence contains three or more polymorphic sites, linkage between all three sites can be simultaneously determined using pooled mixtures of probes, each pool containing three probes. If each of three polymorphic sites has two polymorphic forms, then there are 2 ×2×2 combinations of polymorphic forms, and eight pools of three probes each are required. The hybridization patterns of these more complex arrays are interpreted in similar manner to that discussed above for single polymorphic sites with two forms. In the general case, when such an array is hybridized to a homozygous target molecule, a single pooled probe mixture has a combination of probes matched with the target molecule and shows the highest binding to the target. When the array is hybridized with two heterozygous target molecules, two pooled probe mixtures having component probes matched with target segments in the same molecule show highest binding. Other pooled probe mixtures show varying degrees of lesser binding depending on how many component probes, if any, are matched with a segment of one of the target molecules.

In addition to pools of probes, arrays for linkage analysis sometimes contain additional cells occupied with single species of probes. These probes are of the same composition as the probes contained in the pooled mixtures, and serve as controls to assess cooperative binding of targets to pooled mixtures. If all probes in a pool are complementary to segments on a single target molecule, then cells occupied by individual probes from the pool should show specific binding to the target, but the aggregate of specific binding (normalized if appropriate to accommodate differences in probe deposition among other factors) should be less than the binding to the pooled probe position. By contrast, if all probes in a pool are complementary to a segment of a target, but the different probe are complementary to segments in different target molecules, the binding of the target to a pool of matched probes is greater than the aggregate of binding of target to cells of individual probes (after appropriate normalization). The relative binding of a target to pooled probes with the aggregate of binding to the components probes of a pool therefore serves to provide confirmation of target assignments based on comparisons of the relative binding of target to different pools of probes.

Additional confirmation of target assignments can be obtained by comparing binding of intact target molecules containing two or more segments matched with a pool of probes, with control substrates containing only one of segments. Optionally, target and control substrates are differentially labelled to allow simultaneous application to an array. Target and controls are also optionally diluted to equalized label intensities before application to the array. An intact target molecule shows stronger binding to a pooled mixtures of probes matched with segments of the target than does the mixture of control substrates (with normalization to eliminate effects due to different amounts of target, if needed). The intact target and the mixture of control substrates bind to approximately the same extent to arrays occupied by individual probes from the pooled mixture. The pattern of relative binding of target and controls to pools of probes and to individual component probes of pools, thus can provide further confirmation that linkage has been correctly assigned in a target.

The principles that are used to analyze linkage in a single target sequence can be expanded to design an array that can analyze linkage in any number of target sequences, including, if desired, all or substantially all sequences in the human genome. Such an array contains a group of several cells occupied by pooled probes, optionally with additional cells occupied by single probes, for each target sequence. Each group of cells is then analyzed independently in the manner described above.

b. Use of Pooled Probes for Expression Monitoring

General methods for using arrays of probes for monitoring expression of mRNA populations are described in PCT/US96/143839 and WO 97/17317. Such methods employ groups of probes complementary to mRNA target sequences of interest. An mRNA populations or an amplification product thereof is applied to such an array, and targets of interest are identified, and optionally, quantified from the extent of specific binding to complementary probes. Optionally, binding of target to probes known to be mismatched with the target can be used as a measure of background nonspecific binding and subtracted from specific binding of target to complementary probes.

The present methods employ arrays having at least some cells occupied by pooled probe mixtures for expression monitoring. In at least some of the pools, the two (or more) component probes are both complementary to nonoverlapping segments of the same target sequence. The spacing and base sequence of the segments can be selected to optimize specific binding due to base composition effects and cooperative binding effects. The presence of a target is detected by specific binding of the target to pooled probe mixtures containing component probes complementary to the target. Optionally, such binding can be compared with binding of pooled mixtures of probes in which one or both component probes contains a mismatch with a target of interest. Binding of mismatched probe pools serves as a measure of background and can be subtracted from binding of matched pooled probes. A significant difference in binding between a pool of perfectly matched probes and a pool of mismatched probes signifies that the mRNA to which the matched probes are complementary is present. Binding to the pool of perfectly matched probes is typically at least 1.2, 1.5, 2, 5 or 10 or 20 times higher than binding to the mismatched probes. Use of pooled probes in expression monitoring methods can increase the ratio of signal to background and therefore result in greater sensitivity and/or greater accuracy in quantitative measurements of mRNA levels. Such methods are particularly valuable with complex mixtures of target sequence (e.g. total mRNA populations, total genomic DNA) [14, 15]

c. Use of pooled probes in sequence analysis

Target nucleic acids of unknown sequence can be sequenced by hybridization to an array containing all probes of a given length in a process sometimes known as sequencing by hybridization. The subset of specifically hybridizing probes in such an array is identified, and the sequence of the target is assembled from the sequences of these probes (see e.g., EP 562047). One potential limitation of such methods is that segments of target sequence commensurate with the length of probes typically used for hybridization assays recur with significant frequency in a target sequence. Such recurrence limits the length of target sequence that can be applied to an array, and/or complicates interpretation of the hybridization pattern of an array.

The present methods provide a solution to this problem using pooled probe mixtures. In the present methods, an array of probes is constructed which comprises a number of subarrays of pooled probed mixtures. The pools in each subarray have one common probe, and one variable probe. Collectively, the variable probes in a subarray constitute all probes of a given length. The common probes vary between the different subarrays. The common probes are chosen to be complementary to known regions of target sequence flanking regions to be sequenced. For example, if one is sequencing a chromosome, the common probes can be designed to be complementary to known markers distributed at fairly regular intervals throughout the chromosome.

Optionally, the target sequence can be fragmented before application to an array, although any fragmentation should leave intact linkage of marker regions to flanking DNA to be sequenced. After hybridization of target sequence to the array, binding to the probes in the different subarrays is determined. A region of target sequence is then compiled from each subarray from the oligonucleotides showing specific binding in that subarray. Each region of target sequence read from a subarray is mapped as being in proximity to the marker complementary to the common probe included in pooled mixtures in that subarray. Accordingly, the present methods allow simultaneous sequencing and mapping of numerous segments of a target sequence.

(e) Use of Pooled Probes in Resequencing Array

As noted in the Background Section, WO 95/11995 describes methods of resequencing involving comparison of binding of four probe sets to a target. One probe set contains overlapping probes that span a reference sequence and are complementary to the reference sequence. The other probe sets contain corresponding probes for each probe in the first set, except at an interrogation position, at which corresponding probes from the four probe sets differ. Corresponding probes are often arranged physically or conceptually as a column on a support. Binding of target to a column of four corresponding probes is compared, and a base in the target sequence is assigned as the complement of the base occupying the interrogation position of the probe showing the highest specific binding to the target sequence.

Such methods can also be performed using pooled probe mixtures rather than single probes. The components of such probe mixtures can be viewed as first and second groups of probes, each mixture having one probe from the first group and one probe from the second group. The first group of probes contains the same four probe sets as described in WO 95/11995. The second group of probes contains probes that are complementary to the reference sequence and allow cooperative binding with a partner probe from the first group.

Each of four corresponding probes in the first group is usually matched with the same partner probe from the second group. The partner probe is designed to be complementary to a segment of target DNA that does not overlap the segment to which the four corresponding probes are complementary but is sufficiently proximate to allow cooperative binding between two probes in probe mixtures. Optionally, the segments of DNA bound by the partner probe and the four corresponding probes can be immediately adjacent (i.e., with no intervening bases).

Different columns of four corresponding probes from the first group can be matched with the same or different partner probes. For example, in some arrays, each of the columns of four corresponding probes is matched with the same partner probe. In other methods, columns of corresponding probes are matched with different partner probes such that the separation of target segments bound by partner probes and corresponding probes remains constant. Alternatively, different columns of four corresponding probes from the first group can be matched with different partner probes without a constant separation between segments bound by the probes in a pooled mixture.

In all of the above arrangements, binding of pools is compared for four pools containing four corresponding probes from the first group. A base in the target sequence is identified as the complement of the base occupying the interrogation position of the pool showing highest binding. Comparison of pooled probes in this manner can offer a higher ratio of binding of matched to mismatched pools, thereby increasing the accuracy of assignment of bases in the target sequence.

(f) Measuring Sequence Length

The incremental normalized binding of a target to pooled probes matched to the target relative to the aggregate binding to components of the pool is related to the separation of target segments bound by the probes. As the spacing increases, co-operative binding decrease, as does the incremental binding of target to a pooled probe mixture. These binding characteristics can be used to assess the length of a segment of unknown length flanked by two know markers. For example, the segment of unknown length can be a restriction fragment length polymorphism including di, tri and tetranucleotide repeats.

An array is designed containing a pooled probe with two component probes complementary to markers flanking a sequence whose length is going to be analyzed. Also present in the array are control cells containing each of the pooled probes without the other. The array is then calibrated for a series of control substrates in which the known markers are separated by different known lengths of intervening sequence. For each control substrate, a ratio is determined between binding to the pooled probe mixture and the aggregate of binding to individual probes. This ratio can then be plotted as a function of intervening sequence length. As the intervening sequence length increases, the ratio of binding decreases toward unity.

The array is then hybridized with a target to be analyzed containing the two known markers separated by an intervening segment of unknown length. The ratio of binding of target to pooled and control probes is determined as before. The length of the intervening segment can then be read from the plot or by computerized interpolation. This type of analysis is particularly useful in assessing the length of trinucleotide repeats which are associated with several genetic diseases, such as Huntington's disease.

(g) Order of Fragments

In genomic sequencing or restriction mapping, one sometimes knows that a target sequences is comprised of several specific component segments, but does not know the order of the segments. For example, one might know that a target sequence has component sequences a, b and c, but not know whether the order of the sequences is abc, acb, or bca. The order of the component sequences can be determined by hybridization to an array containing pools of probes, each pool having two component probes hybridizing to different segments, the different pools differing in the combination of segments to which their component probes hybridize.

In general, segments of a target sequence that are closer together show greater cooperativity in binding to pooled probe mixtures that segments further apart. Thus, for a target sequence abc, a pooled mixture of ab or bc shows stronger binding relative to the aggregate of a+b or b+c than does a pooled mixture of ac relative to a+c. Thus, the relative binding of target to the three pooled probe mixtures relative to the aggregate of binding to appropriate component probes indicates, which target segments are in closet proximity to each other, and thus, the order of segments in the target sequence.

A potentially interesting application is sequence reconstruction (contig assembly) in sequencing by hybridization (SBH). One of the major obstacles to using short DNA probes for SBH is the presence of repeated sequences. De novo SBH utilizes an array of the set of all probes of length n (usually 6–10) to determine the presence of length n subsequences in the target of interest. These subsequences are compared to each other and aligned to reconstitute the contiguous target sequence. Repeated regions of length n or longer complicate the sequence reassembly, since it is no longer possible to unambiguously determine the linkage of sequences on either side of the repeat. It has been proposed that measuring the distance between reference points in a sequence could increase the possible fragment length an array can resequence by more than 4-fold [16] It is now possible to assess experimentally the distance between reference points by testing combinatorially a large number of alternative probe pairings. For example, if there are three contigs a, b, and c, of possible order a-b-c or a-c-b, the order can in principle be established by hybridizing the target to the pairwise probe combinations a-b and a-c. In addition, it may be necessary to compare hybridizations of the target fragmented to various extents, e.g. with restriction enzymes. Using the principle of Sturtevant [1], sequences close together will be more likely to remain linked.

EXAMPLES MATERIALS AND METHODS

Oligonucleotide Arrays. DNA arrays were synthesized using 5'-MeNPOC protected phosphoramidites [10, 11]. A MeNPOC protected hexaethylene glycol phosphoramidite is coupled to a glass substrate which has been silanated with bis(hydroxyethyl)aminopropyltriethoxysilane. The substrate is then exposed to 365 nm light through a lithographic mask. The MeNPOC protecting group is removed by light, so that only the exposed sites become available for coupling. Repeated cycles of light-directed deprotection and nucleoside base coupling allow the efficient parallel synthesis of any desired combination of large numbers of different oligonucleotides.

Paired probe array synthesis. Paired arrays are synthesized in a similar fashion (FIG. 1). The primary difference is that prior to coupling the first nucleoside the array surface is exposed for one half-life of the MeNPOC protecting group, resulting in an approximate 1:1 mixture of protected and deprotected sites. The deprotected sites are coupled with a 5'DMT protected nucleoside. The DMT group is stable through the photodeprotection and synthesis cycles. The remaining MeNPOC protected linker is patterned as described above into a probe array (array of probe #1). Upon completion, these probes are capped (either with 1:1 Acetic Anhydride, N-Methylimidazole in Lutidine, THF, or by coupling of N, N Diethyl N,N diisopropyl phosphoramidite) to prevent further elongation. After the first probes are synthesized and capped, the DMT protected sites are deprotected (3% TCA/DCM, 30s), and a MeNPOC protected linker is coupled onto these sites. The second set of probes is then patterned onto these sites using MeNPOC photochemistry; the result is an array with a mixture of two different DNA probes at every location.

Labeled DNA Targets. DNA oligonucleotides bearing a 5' terminal fluorescein label were synthesized on solid supports using standard phosphoramidite chemistry. Oligonucleotides 10c-27c, 10g-27t, 10c-27t, and 10g-27c are based on the sequence 5'-Fcc act cac gNg agc tct cca tgc att Ngg tat ttt cgt ctg gga ggt atg cac gcg ata gca, (SEQ ID NO:1), where F denotes fluorescein. The letter N indicates positions 10 and 27. The base at these positions is indicated in the name of each oligonucleotide. Likewise, oligonucleotides 10c and 10g are based on the sequence 5'Fct cac gNg agc tct c, (SEQ ID NO:2), and 27c and 27t are based on 5'F tgc att Ngg tat ttt (SEQ ID NO:3). The 10c, 10g, 27c, and 27t sequences were derived from the position 10 and 27 double variants listed above. In addition to the oligonucleotide targets, human mitochondrial DNAs of 160 bases and 2.5 kb were prepared using single-stranded asymmetric PCR. These DNAs were amplified from samples previously sequenced on an ABI 373A DNA Sequencer. Labeling was by incorporation of biotin-16-dUTP during PCR. Two 2.5 kb amplicons were prepared, differing at three positions. Amplicon 1 had the sequence 93c-1438c-2131a. Amplicon 2 had the sequence 93t-1438t-2131g.

RESULTS

Figure 2:
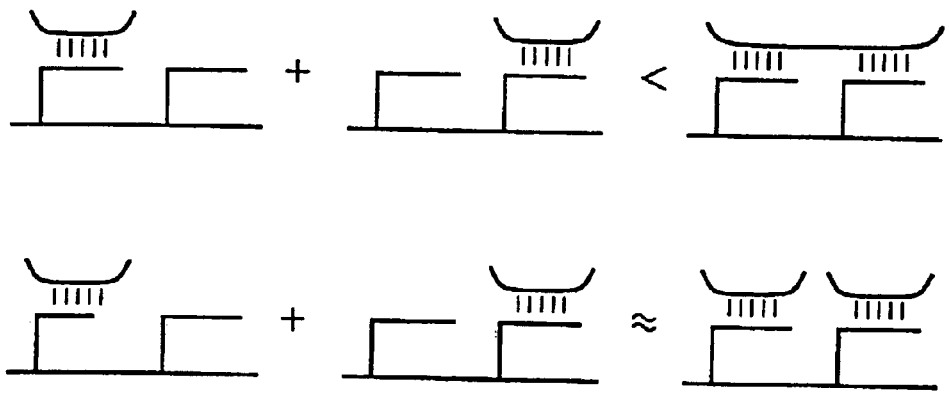
FIG. 2. Cooperative hybridization distinguishes between physically linked and unlinked target sequences. Two different probe sequences (blue and pink) are synthesized at the same address on the oligonucleotide array, as described in Materials and Methods. Complementary target sequences (green and purple) are hybridized separately; together but unlinked; or linked in a single molecule. A) Individual targets hybridize less strongly than linked targets, which hybridize cooperatively. Therefore, the sum of the hybridization signals from two individual targets is less than the signal from the linked targets. B) The sum of the hybridization signals from each individual target hybridized separately is expected to be similar to the signal from the two unlinked targets hybridized together.

Cooperative hybridization and linkage detection. To determine whether cooperative hybridization could be used to distinguish between linked and unlinked pairs of otherwise identical sequences, we designed a simple experiment to assay for linkage between a pair of 9-mer sequences separated by 8 nucleotides. The principle is illustrated in FIG. 2.

Figure 3:
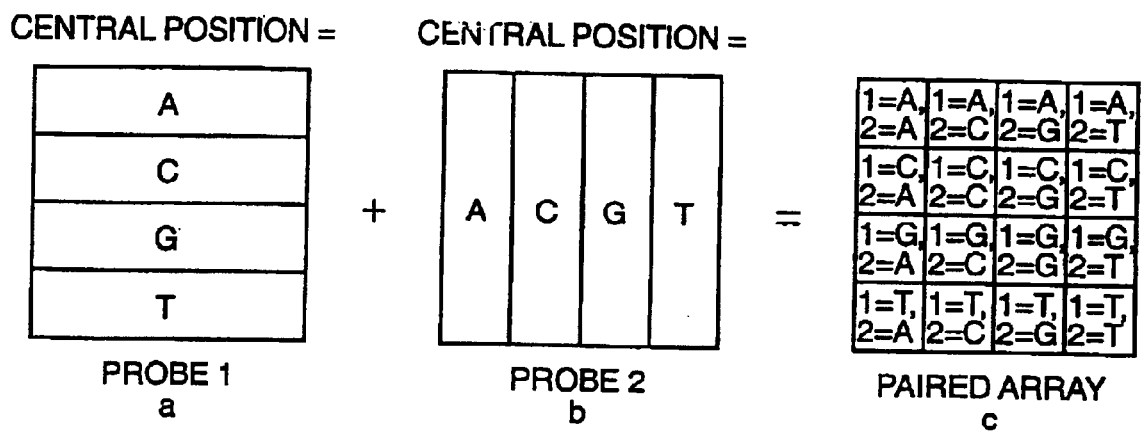
FIG. 3. Design and layout of a paired probe array. A) Probe 1 was synthesized in four 400 μm×1600 μm rectangles, with the central position $N_1$=A, C, G, and T in the successive rectangles. B) Probe 2 was synthesized in four 400 μm×1600 μm rectangles perpendicular to the Probe 1 rectangles on the same region of the substrate. The Probe 2 central position $N_2$=A, C, G, and T in successive rectangles. C) The resulting array contained 16 sites, each with a different combination of $N_1$ and $N_2$ in the two probes.

A 4×4 array was synthesized, in which each 400 µm×400 µm site contained a mixture of two different 9-mer probe sequences, Probe 1 (3'-gtgcN1ctcg-5')(SEQ ID NO:4) and Probe 2 (3'-gtaaN2ccat-5')(SEQ ID NO:5). To demonstrate that any cooperative effect was sequence-specific, we designed the array to include four variants of each of the probes, in which the central base of Probe 1 and Probe 2 was substituted with A, C, G, or T. The resulting array contained 16 sites. Each site contains a different combination of N1 and N2 for the two probes. In this way all sixteen mixtures of Probe 1-N1 and Probe 2-N2 were synthesized (FIG. 3).

Two sets of hybridizations were performed. First, physically linked targets complementary to Probe 1 and Probe 2 were hybridized to the array. If pooled probes could hybridize in a cooperative manner to two pooled probes, the signal from an array containing two pooled probes would be greater than the sum of the non-cooperative hybridization signals in the regions where only one probe perfectly matched the target. Second, as a control, independent targets matching each of the probes in a mixture were hybridized to the array. In this case, it was expected that the hybridization signal in the areas where two targets had perfectly matching probes would approximate the sum of the hybridization signals in the regions where only one or the other target had a perfect match (FIG. 2).

Figure 4A:
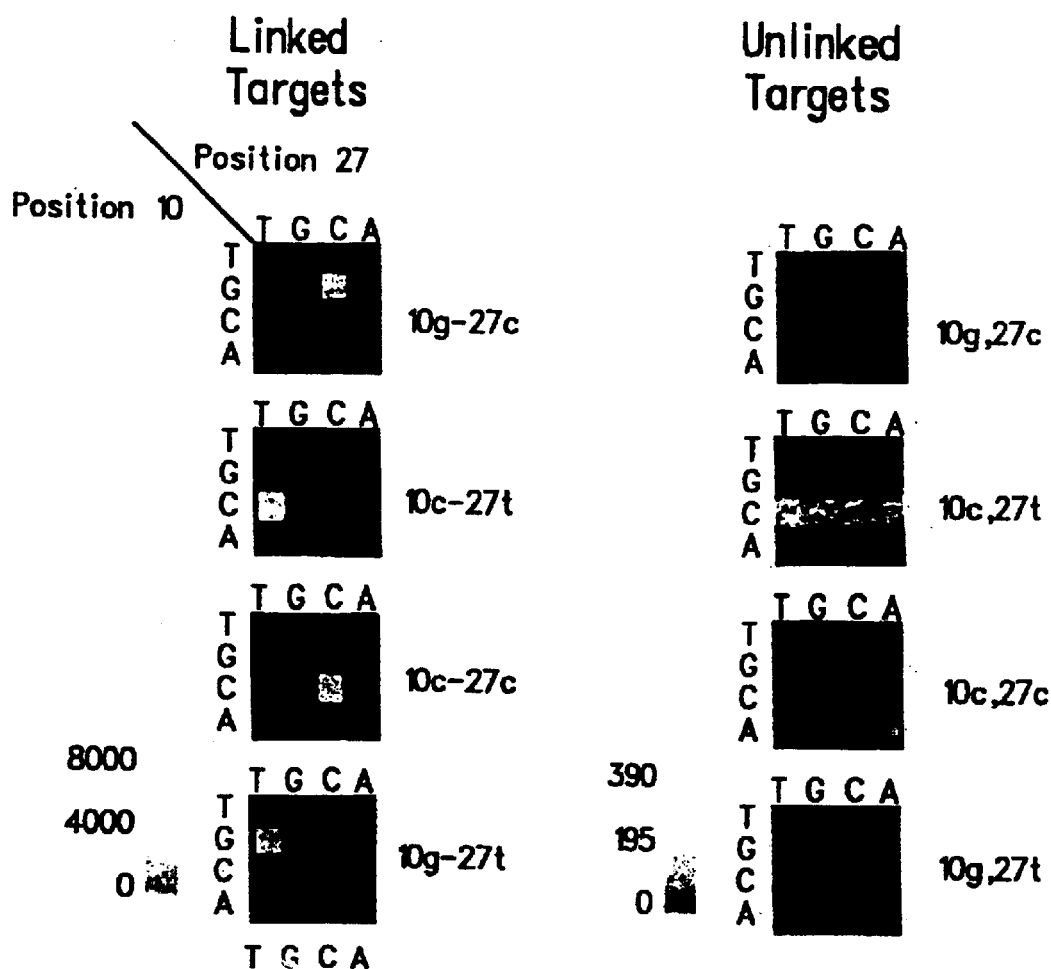
FIG. 4A. Fluorescence images of cooperative vs. noncooperative hybridization to paired probe arrays. The design of the array is shown in FIG. 3. Unambiguous hybridization to the double perfect match probe pair is shown for four different linked sequence pairs (10g-27c, 10c-27t, 10c-27g. and 10g-27t from top of left hand column) (SEQ ID NO:1). Hybridization images of the corresponding unlinked targets are shown in the adjacent right hand column.
Figure 4B:
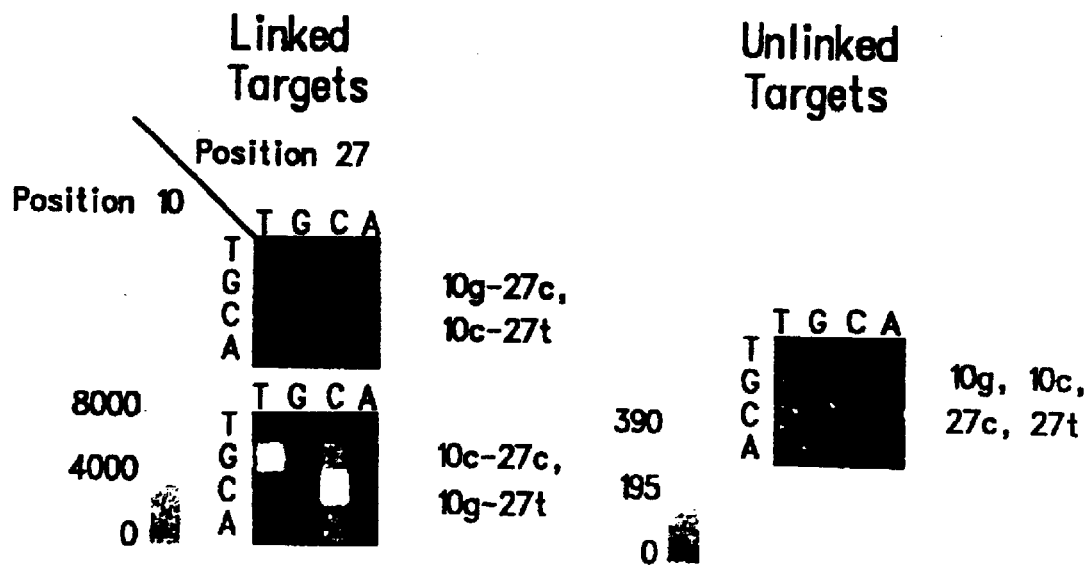

Hybridizations were performed as described in Table 1. Different mixtures of DNA target complementary to Probe 1 and Probe 2 were used to investigate the extra stability of the paired hybridization (FIG. 4A). The fluorescence intensity of the linked targets was always greater than 40× the intensity of their unlinked counterparts. The intensities of the linked targets in the regions where they matched both paired probes were 2–3× the sum of the intensities where they matched just Probe 1 or Probe 2. For the unlinked targets, the intensities in the regions where the targets matched both paired probes was 15–35% less than the sum of the regions where they matched Probe 1 or Probe 2. This 15–35% loss of signal may be due to crowding effects at the surface, since almost twice as much target is present in the regions where the targets match both probes. The discrimination ratio between the correct calls and single base changes was also markedly better with the linked targets. These results demonstrate the cooperative hybridization of linked target sequences to paired probes. In every case, the linkage or independence of N1 and N2 was clearly distinguished, and the variable bases at N1 and N2 were correctly determined in the physically linked targets.

Assignment of linkage in a heterozygous mixture. To determine if hybridization to paired probe arrays could be used to assign linkage directly in complex heterozygotes, two further experiments were conducted. In each case, equimolar mixtures of two linked targets were hybridized to a 9-mer paired probe array. In the first experiment, the mixture consisted of 10c-27t and 10g-27c. In the second experiment, the mixture was of 10g-27t and 10c-27c. Although the two experiments have targets that are identical in sequence composition, the pairing is different. The results are shown in the left-hand bottom two panels of FIG. 4A. In each mixture, it was straightforward to assign linkage. In each case, the linked sequences are clearly discriminated from the other possible arrangements (e.g. c—c, g-t vs. g-c, c-t). Even though the probes in the four array positions c—c, c-t, g-c, g-t are complementary to equimolar amounts of target in the hybridization mixture, there is significantly more signal where the two probes are perfectly complementary to the same target molecule (1.4–7×intensity). Furthermore, the control hybridization, in which unlinked targets have the same sequence composition as the linked targets, shows lower signal and no evidence of cooperativity. These results show that paired probe arrays can be used to assign linkage in mixtures containing two different multiply polymorphic alleles.

Cooperative hybridization over distances of more than 2 kilobases, and construction of SNP haplotypes. To examine the strength and specificity of linkage over a greater distance, we synthesized paired probe arrays with the probe sequences chosen from different regions of a 2.5 kb mitochondrial DNA amplicon. The length of the probes was increased to 30-mers to allow hybridizations to be performed under more stringent conditions. Higher stringency was used to reduce the secondary structure in the targets and to favor cooperative hybridization by destabilizing individual hybridizations.

Figure 5A:
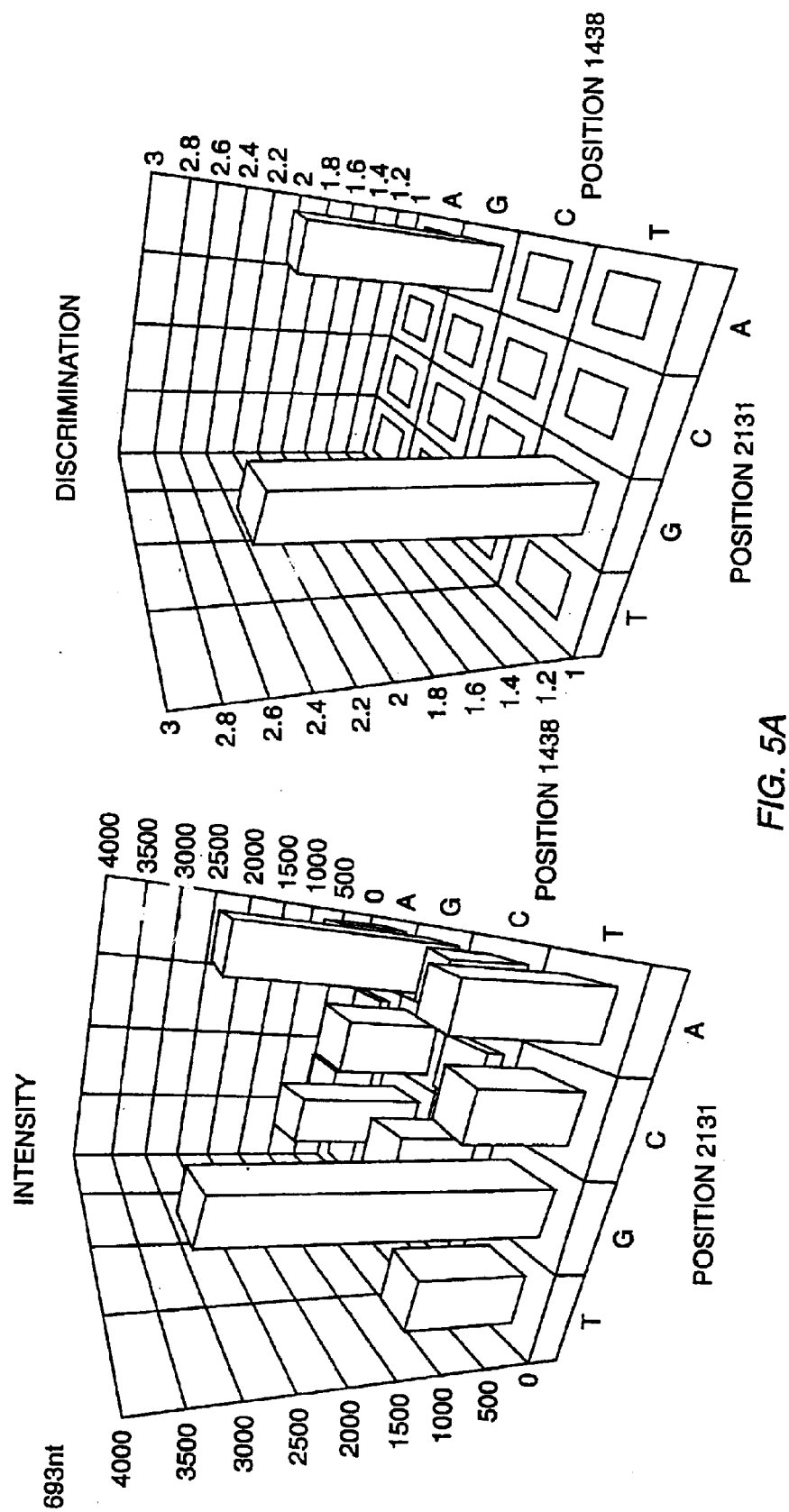
FIG. 5. Cooperative hybridization and assignment of linkage between SNPs separated by 693, 1345, and 2038 nucleotides. Targets are 50:50 mixtures of two 2.5 kb amplicons that differ in sequence at positions 93, 1438, and 2131. The arrays are synthesized as described in FIG. 3, except that the probes are 30-mers with the variable base 15 nt from the 3' end. A) Left panel: background corrected intensities from a paired probe array interrogating positions 1438 and 2131 in the 2.5 kb amplicons. The 50:50 target mixture contains 1438g-2131t and 1438a-2131c. The linkages can be assigned unambiguously from the hybridization patterns. Probe 1 on the array is complementary to positions 1424–1448, Probe 2 is complementary to positions 2117–2141. Right panel: discrimination plot of the same hybridization. B) Interrogation of positions 93 and 1438. The 50:50 target mixture contains 91t-1438t and 91c-1438c. Probe 1 complements positions 79–103. Probe 2 complements positions 1424–1448. C) Interrogation of positions 93 and 2131. The 50:50 target mixture contains 91g-2131t and 91a-2131c. Probe 1 complements positions 79–103. Probe 2 complements positions 2117–2141.
Figure 5B:
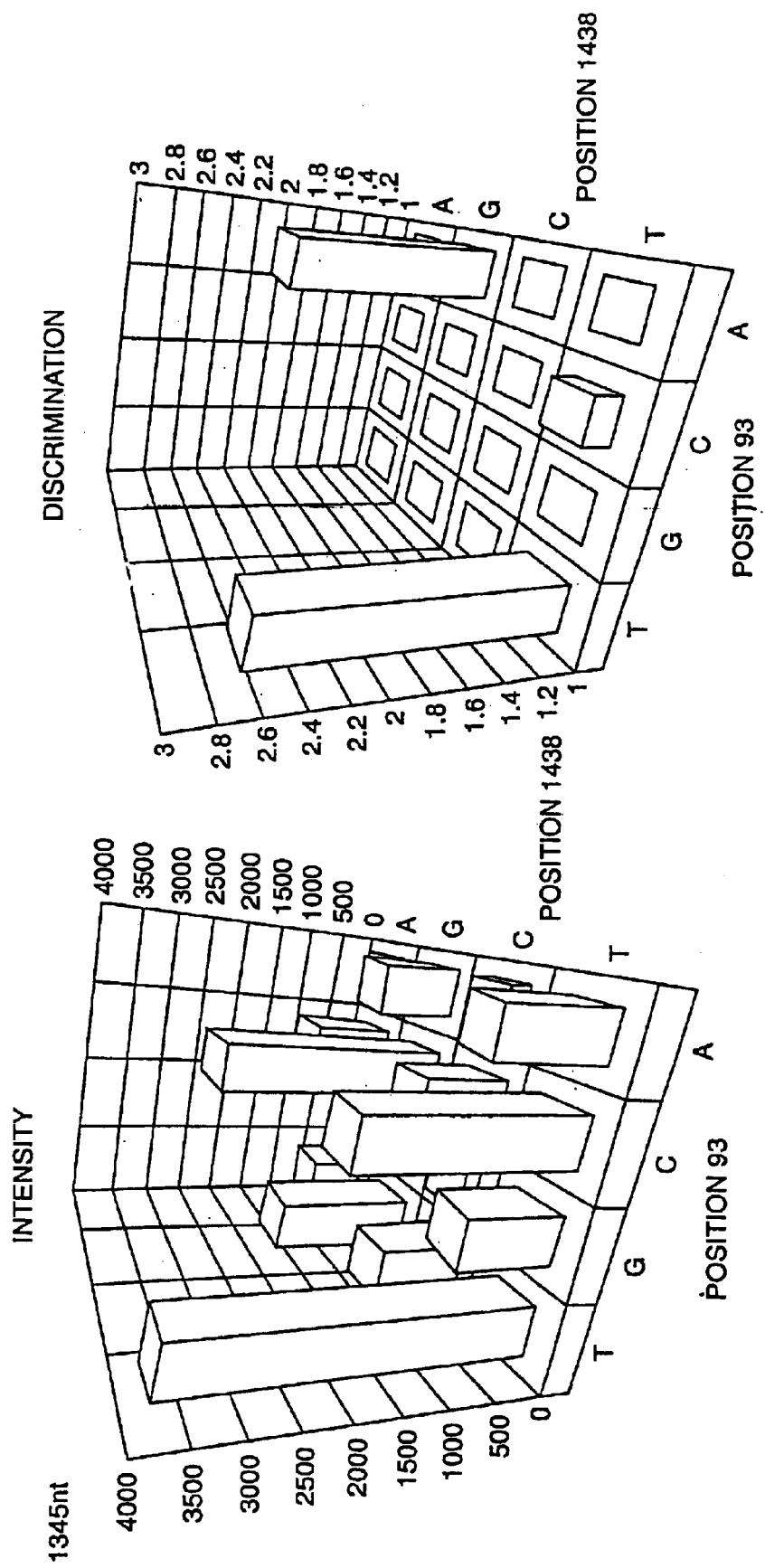
Figure 5C:
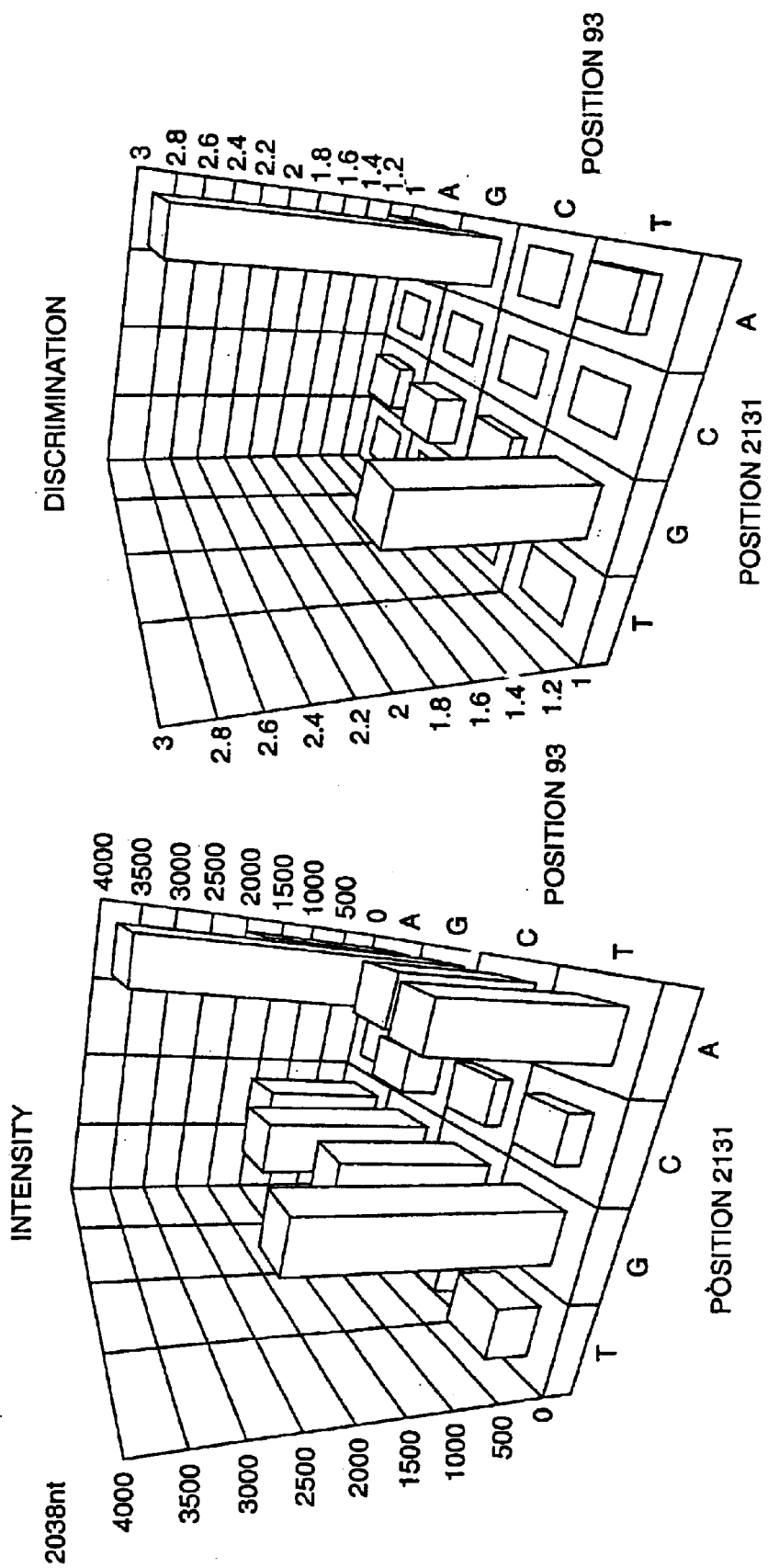

Arrays of three different designs were synthesized. In each design a different pair of single nucleotide polymorphisms (SNPs) was interrogated. In each of three experiments shown, a 50:50 mixture of two 2.5 kb target amplicons was analyzed on a paired array (FIG. 5). The two 2.5 kb amplicons are from the identical region of human mitochondrial DNA, but are polymorphic and differ from each other at the specific sites analyzed by the arrays. In the first experiment, SNPs at positions 1438 and 2131, separated by 693 nucleotides, were analyzed. The second experiment queried SNPs 1345 nucleotides apart, at positions 93 and 1438. The third experiment queried SNPs 2098 nucleotides apart, at positions 93 and 2131. In each experiment, the correct probe cells have the highest intensity (FIG. 5). The results show single base mismatch discrimination and linkage detection between loci separated by distances up to 2.1 kb, although the discrimination was better with the 9-mer paired probe array. This is not surprising, as the discrimination is based on differences of 2 bases out of 50, as opposed to 2 bases out of 18 in the 9-mer experiments.

The data were then analyzed by comparing each probe pair to its 6 single base alterations (the 3 single base changes in Probe 2, keeping Probe 1 constant, and the 3 single base changes in Probe 1, keeping Probe 2 constant) (FIG. 5, right hand column). In this analysis, the distinction between the correct linkage assignments and the incorrect ones is even more apparent. A score of 1 on the discrimination chart means the intensity at that position on the array was the same as the average intensity of all its one base alterations. I.e., the discrimination score for the probe pairing a-a=(a-a)/((a-c+ a-g+a-t+c-a+g-a+t-a)/6). All of the incorrect linkage assignments are close to or less than 1, while the correct linkage assignments produce values of 1.8 or greater. As with the 9-mer paired probe array, the correct linkage assignments (93c-1438c, 93t-1438t, 1438c-2131a, 1438t-2131g, 93c-2131a, and 93t-2131g) were easily distinguished from the incorrect phase (93c-1438t, etc.). Finally, by combining the data from the pairwise experiments, the two haplotypes 93c-1438c-2131a and 93t-1438t-2131g can be unambiguously reconstructed.

Sequence independence of cooperative effect. The experiments described above were carried out using a small number of specific pairs of sequences. We designed two more arrays to investigate cooperative hybridization with a much larger number and variety of different sequences. The aim was to determine to what extent the cooperative effect we observed was sequence-dependent to assess if it could be extrapolated to a larger set of probes.

In the first experimental design, six different 12-mer sequences were each paired with a resequencing array containing eighty-six overlapping 15-mer probes. Therefore, each of these resequencing arrays contained a constant 12-mer sequence to act as an "anchor" for the target, which was queried by the variable 15-mer probes in the array. Each 15-mer was represented by 4 single-base substitutions (A, C, G and T substitutions at the central position) to give a total of 2064 combinations (6 anchors×86 probes×4 substitutions). Of these, 516 were perfect matches to both probes in the pair, and the remainder contained a single base mismatch at the central position in the 15-mer probe.

Figure 6:
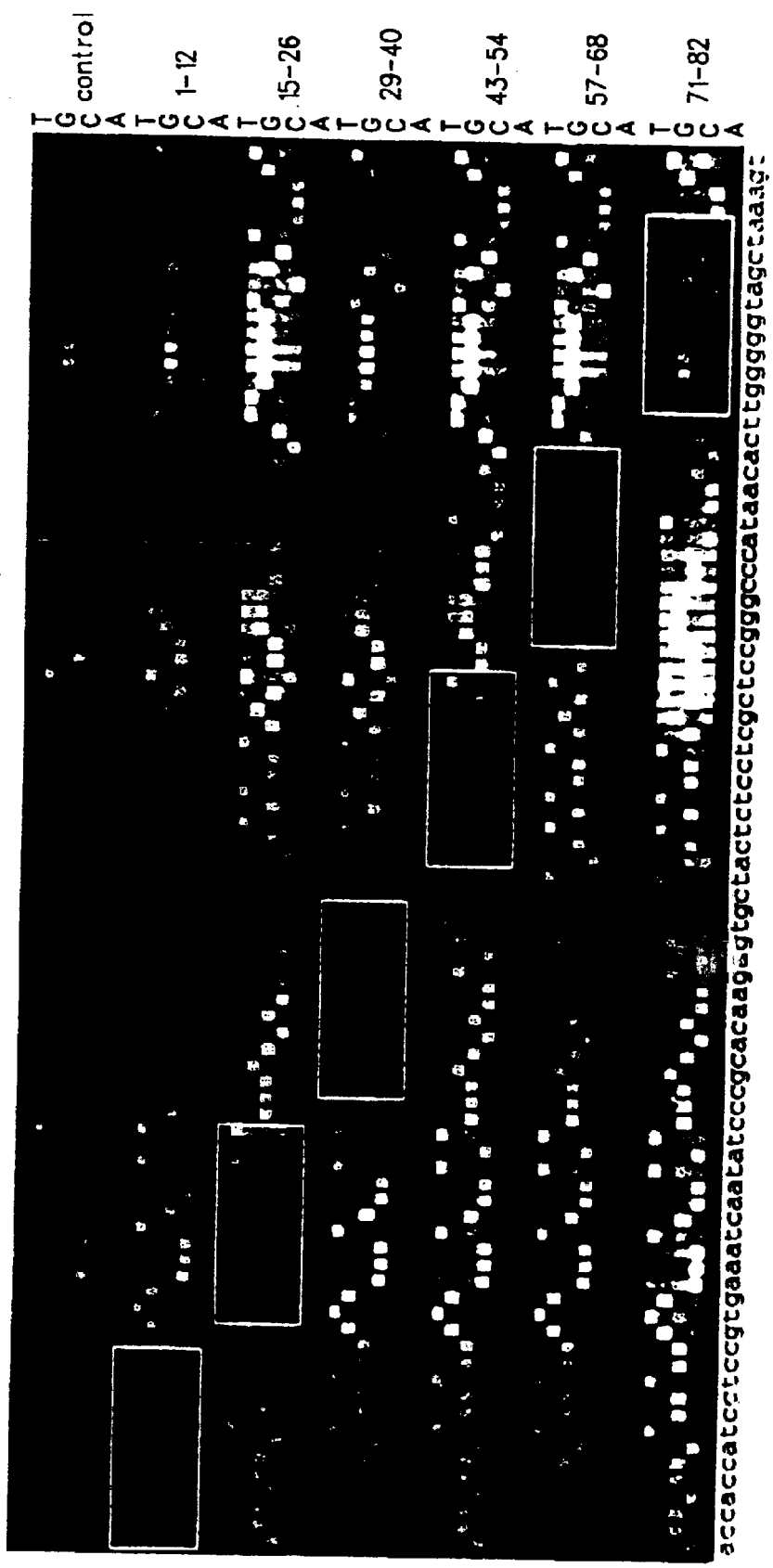
FIG. 6. Effect of pairing six different anchor probes with a resequencing tiling array. In each of the seven tilings shown, 86 columns of overlapping probes step through a region of human mitochondrial DNA in single-base increments 14. Each column contains four 15-mer probes with a central A, C, G or T substitution (indicated to the right of each tiling). Each column of 4 probes therefore contains a perfectly complementary probe as well as 3 single base mismatch probes to the mitochondrial target DNA sequence. The seven repetitions of this 344 unit array (86×4) are arranged as follows: the uppermost tiling is the unpaired control (ie 15-mer probes only); the six subsequent tilings contain constant 12mer probes complementary to positions 1–12, 15–26, 29–40, 43–54, 57–68, 71–82 respectively (labeled in the figure). The regions where the 12-mer anchor sequence overlaps the 15-mer interrogation probe sequence are outlined in white.

A 160 nt fluorescein-labeled amplicon was hybridized to the array, and an image of the hybridization pattern was obtained (FIG. 6). The array included an unpaired tiling as a control. Every paired tiling gave greater signal than the control tiling. The extent of this improvement, in overall intensity and discrimination, is related to the hybridization strength of the region represented by the constant 12mer anchor sequence. For example, positions 1–12 have very low intensity in the control tiling, and anchor 1–12 has a small effect on the intensity and specificity of the hybridization in its paired tiling. Positions 15–26 perform well in the control, and have a dramatic impact as an anchor sequence. No signal increase was expected in the regions where interrogation probe sequences overlap with the anchor sequence (outlined in FIG. 6), because each target molecule cannot hybridize to more than one probe in these cells.

The results showed that a variety of different anchors can be paired with the same resequencing tiling with similar effect; that a given anchor sequence can pair cooperatively with a variety of different sequences at various distances from the anchor; and that signal enhancement by the anchor probe is related to the hybridization strength of the anchor sequence.

To extend these observations and to examine probe-anchor interactions over greater distances, we next paired a single 20-mer anchor probe with a 20-mer tiling array interrogating 2544 nucleotides of the human mitochondrial genome. Two separate arrays were synthesized. The first contained only the 10,17620-mers (2544×4 substitutions per position) as a control. In the second array each cell was a mixture of one of the 10,176 probes and the 20mer complementary to positions 1427–1446 on the amplicon.

Figure 7:
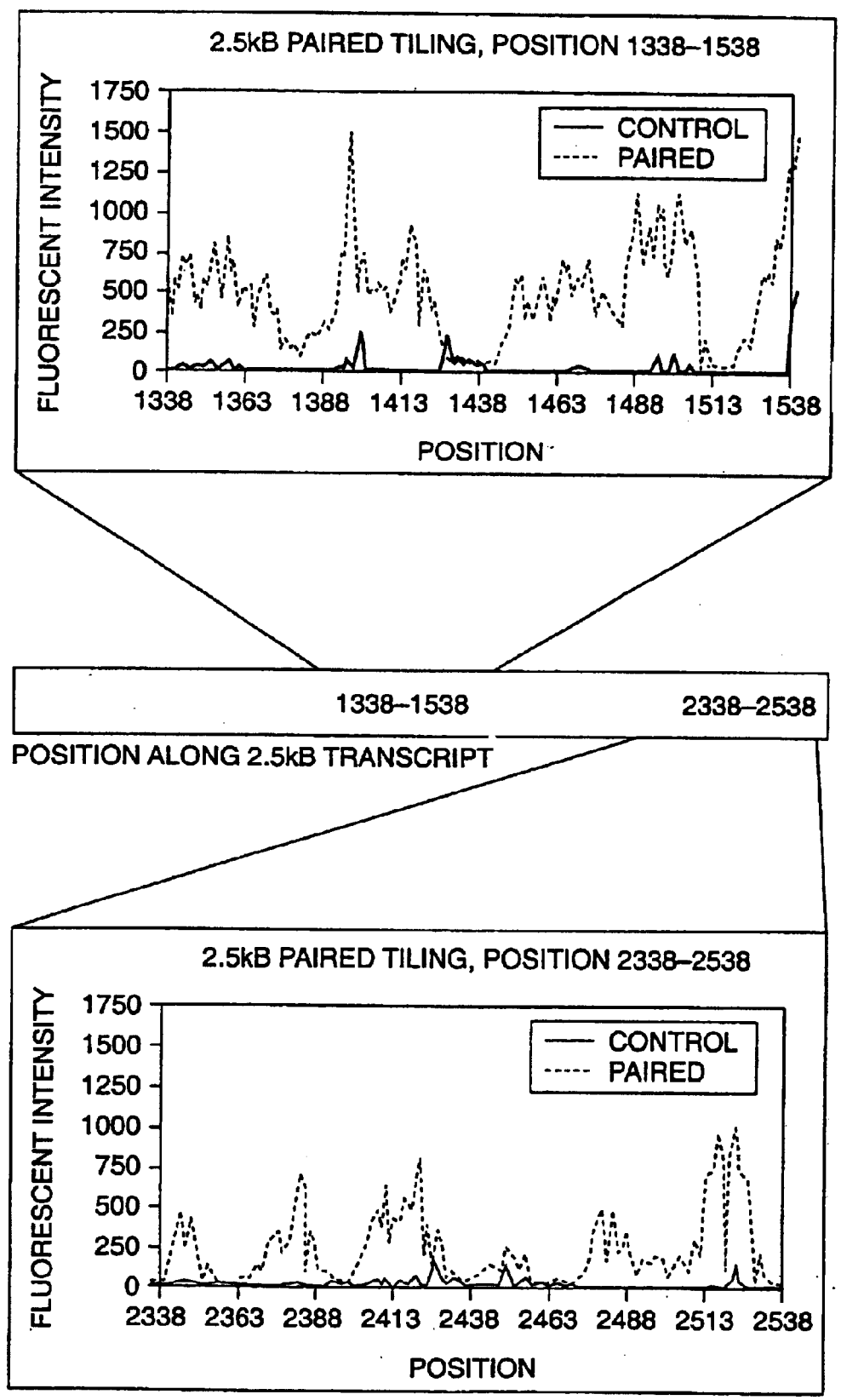
FIG. 7. Comparison of signal intensities obtained from a paired and unpaired array designed to resequence 2.5 kb of human mitochondrial DNA. A 2.5 kb biotin-labeled ssDNA amplicon was hybridized to paired and unpaired resequencing arrays of 20-mer probes. Intensities of perfect match probe cells from two representative portions of the array are plotted vs. position in the target sequence. The 20-mer anchor sequence in the paired array is derived from positions 1427–1446. Signal and discrimination are substantially increased in the paired array vs. the unpaired array.

An analysis of signal intensities versus position in the 2544 base sequence reveals the characteristic dip in the region where the anchor overlaps with the variable probe, and increased signal intensity and discrimination elsewhere on the array (average of 15× fluorescent intensity over the unpaired control) (FIG. 7). At separations greater than 1000 bases between the anchor and probe sites on the target, a strong cooperative binding effect can still be seen. Under the conditions used, 97% of the sequence (2459 out of 2544 bases) could be determined by simply identifying the probe with the greatest intensity in each set of A, C, G, and T substitution probes. In contrast, under these stringent conditions, only 84% of the sequence (2128 bases) could be determined on the unpaired control array.

TABLE 1

TABLE AND FIGURE LEGENDS
Hybridization Experiments

| Array | Target | Conc/ nM | Buffer | Temp/ C. | Time/ h | Label |
|---|---|---|---|---|---|---|
| 9-mer PPA | oligo 10a–27b | 10 | A | RT | 0.5 | F |
|  | oligos 10a and 27b | 10 | A | RT | 0.5 | F |
|  | oligos 10a–27b and 10c–27d | 10 | A | RT | 0.5 | F |
|  | oligos 10a, 10b, 27c, and 27d | 10 | A | RT | 0.5 | F |
| 30 mer PPA d = 693 | 2.5 kb amplicon 1, 2 | 0.75 | B | 37 | 48 | P |
| 30 mer PPA d = 1345 | 2.5 kb amplicon 1, 2 | 0.75 | B | 37 | 48 | P |
| 30 mer PPA d = 2098 | 2.5 kb amplicon 1, 2 | 0.75 | B | 37 | 48 | P |
| 86 nt tiling | 160 nt amplicon | 0.5 | A | 37 | 1 | F |
| 2544 nt tiling | 2.5 kb amplicon 1 | 0.75 | C | 40 | o/n | P |

PPA = Paired Probe Array
Oligo targets: a, b, c and d are placeholders for different sequences. Actual sequences are given in FIG. 4A.
Buffer A = 6xSSPE, 0.005% Triton X-100
Buffer B = 2.4M Tetraethylammonium Bromide, 10 mM Tris pH 7.8, 1 mM EDTA, 0.05% Triton X-100
Buffer C = 2.4M Methyltriethylammonium Bromide, 10 mM Tris pH 7.8, 1 mM EDTA, 0.05% Triton X-100
Label: F = fluorescein, P = phycoerythrin-streptavidin PPA=Paired Probe Array Oligo targets: a, b, c and d are placeholders for different sequences. Actual sequences are given in FIG. 4A.

Buffer A=6xSSPE, 0.005% Triton X-100

Buffer B=2.4 M Tetraethylammonium Bromide, 10 mM Tris pH 7.8, 1 mM EDTA, 0.05% Triton X-100

Buffer C=2.4M Methyltriethylammonium Bromide, 10 mM Tris pH 7.8, 1 mM EDTA, 0.05% Triton X-100

Label: F=fluorescein, P phycoerythrin-streptavidin

Bibliography

1. Sturtevant, *J. Exp. Zool.* 14, 43 (1913).

2. Cox et al., *Science* 250, 245–250 (1990).

3. Dear & Cook, *Nucleic Acids Research* 17, 6795–6807 (1989).

4. Dear & Cook, *Nucleic Acids Research* 21, 13–20 (1993).

5. Ruano & Kidd, *Nucleic Acids Research* 17, 8392

6. Jeffreys et al., *Cell* 60, 473–485.

7. Grace et al., *Human Mutation* 6, 232–242 (1995).

8. Beer & Moudrianakis, *Proc. Nat. Acad. Sci., USA* 48:409–416 (1962).

9. Wiegant, J. et al., *Hum. Mol. Gen.* 1:8 587–591 (1992)

10. Fodor et al., *Science* 251, 767–773 (1991).

11. Pease et al., *Proc Natl Acad Sci USA* 91, 5022–5026 (1994).

12. Orosz & Wetmur, *Biopolymers* 16, 1183–1199 (1977).

13. Broude et al., *Proceedings of the National Academy of Sciences, USA* 91, 3072–3076 (1994).

14. Chee et al., *American Association For The Advancement Of Science* 274, 465–688 (1996).

15. Lockhart et al., *Nature Biotechnology* 14, 1675–1680 (1996).

16. Lysov, et al, *The Journal of Sequencing and Mapping* 6, 65–73 (1996).

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

---

What is claimed is:

1. An array comprising a plurality of sets of nucleic acid probes, each set comprising a plurality of probe pools bound to a different region of a support, each pool comprising (i) a first probe that is complementary to a known marker located in a target nucleic acid, and (ii) a second probe that differs in sequence from the first probe; and wherein first probes within the same set have the same sequence but first probes in different sets have different sequences.

2. The array of claim 1, wherein the first probes in different sets are complementary to different markers on the target nucleic acid.

3. The array of claim 1, wherein second probes within the same set are the same length and collectively represent all possible sequences having that length.

4. An array comprising a set of nucleic acid probes, the set comprising a plurality of different nucleic acid probe mixtures bound to different regions of a support, each mixture comprising an interrogation probe and a partner probe, wherein
    the interrogation probes are complementary to a first segment of a reference nucleic acid that contains an interrogation position;
    interrogation probes at different regions are identical to one another except at the interrogation position, with interrogation probes at different regions having a different nucleotide base at the interrogation position; and
    the partner probe is complementary to a second segment of the reference nucleic acid that does not overlap the first segment.

5. The array of claim 4, wherein different probe mixtures contain the same partner probe.

6. The array of claim 4, wherein different probe mixtures contain different partner probes that are complementary to different second segments.

7. The array of claim 4, wherein the interrogation probes and partner probes are complementary to first and second segments that are separated from one another on the reference nucleic acid.

8. The array of claim 4, wherein the interrogation probes and partner probes are complementary to first and second segments that are immediately adjacent one another on the reference nucleic acid.

9. A method for analyzing a target nucleic acid sequence, comprising
   (a) providing an array comprising a set of nucleic acid probes, the set comprising a plurality of different nucleic acid probe mixtures bound to different regions of a support, each mixture comprising an interrogation probe and a partner probe, wherein
      the interrogation probes are complementary to a first segment of a reference nucleic acid that contains an interrogation position;
      interrogation probes at different regions are identical to one another except at the interrogation position, with interrogation probes at different regions having a different nucleotide base at the interrogation position; and
      the partner probe is complementary to a second segment of the reference nucleic acid that does not overlap the first segment; and
   (b) applying a sample comprising a target nucleic acid to the array; and
   (c) determining the identity of the nucleotide base at the interrogation position of the target nucleic acid from the relative binding of the target nucleic acid to the different probe mixtures.

10. The array of claim 4, wherein the set of nucleic acid probes comprises four different nucleic acid probe mixturee, with interrogation probes in different mixtures having a different one of the four nucleotide bases at the interrogation position.

* * * * *

SEQUENCE LISTING

<160> NUMBER OF SEQ ID NOS: 5

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Oligo 1
<223> OTHER INFORMATION: 5' Fluorescein Label

<400> SEQUENCE: 1
ccactcacgs gagctctcca tgcattyggt attttcgtct gggaggtatg cacgcgatag    60
ca                                                                   62

-continued

```
<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:Oligo 2
<223> OTHER INFORMATION: 5' Fluorescein Label

<400> SEQUENCE: 2
ctcacgsgag ctctc                                                        15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence:Oligo 3
<223> OTHER INFORMATION: 5' Fluorescein Label

<400> SEQUENCE: 3
tgcattyggt atttt                                                        15

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence:Probe 1
<221> NAME/KEY: MOD_RES
<222> LOCATION: (5)
<223> OTHER INFORMATION: n is A or C or G or T

<400> SEQUENCE: 4 gctcncgtg                                                                9

<210> SEQ ID NO 5
<211> LENGTH: 9
<212> TYPE: DNA
<213> ORGANISM: Artificial Sequence
<220> FEATURE:
<223> OTHER INFORMATION: Description of Artificial Sequence:Probe 2
<221> NAME/KEY: MOD_RES
<222> LOCATION: (5)
<223> OTHER INFORMATION: n is A or C or G or T

<400> SEQUENCE: 5 taccnaatg                                                                9
```